United States Patent
Bonutti et al.

(10) Patent No.: US 9,980,741 B2
(45) Date of Patent: May 29, 2018

(54) METHODS AND SYSTEMS FOR CONTROLLING AN ULTRASONIC HANDPIECE BASED ON TUNING SIGNALS

(75) Inventors: Peter M. Bonutti, Effingham, IL (US); Justin Beyers, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 469 days.

(21) Appl. No.: 13/495,742

(22) Filed: Jun. 13, 2012

(65) Prior Publication Data

US 2012/0316474 A1    Dec. 13, 2012

Related U.S. Application Data

(60) Provisional application No. 61/496,147, filed on Jun. 13, 2011, provisional application No. 61/526,207, filed on Aug. 22, 2011, provisional application No. 61/526,182, filed on Aug. 22, 2011.

(51) Int. Cl.
| | | |
|---|---|---|
| *A61B 17/00* | (2006.01) | |
| *A61B 17/32* | (2006.01) | |
| *A61B 90/00* | (2016.01) | |

(52) U.S. Cl.
CPC ............. *A61B 17/320068* (2013.01); *A61B 2017/00022* (2013.01); *A61B 2090/064* (2016.02)

(58) Field of Classification Search
CPC .. B06B 1/00; B06B 3/00; G10K 11/00; A61B 2017/00106; G01S 15/8906
USPC ............... 600/437, 438, 446, 459; 601/2; 73/584–648; 367/87
See application file for complete search history.

(56) References Cited

U.S. PATENT DOCUMENTS

| | | | |
|---|---|---|---|
| 4,027,559 A | | 6/1977 | Wallrafen |
| 4,651,716 A | * | 3/1987 | Forester ............... A61H 31/006 600/16 |
| 4,750,902 A | * | 6/1988 | Wuchinich ....... A61B 17/22012 604/22 |
| 5,242,385 A | | 9/1993 | Strukel |
| 5,391,144 A | | 2/1995 | Sakurai et al. |
| 5,514,086 A | | 5/1996 | Parisi et al. |
| 5,674,235 A | | 10/1997 | Parisi |
| 5,796,007 A | | 8/1998 | Panagotopulos et al. |

(Continued)

OTHER PUBLICATIONS

Non-Final Office Action dated Jan. 5, 2015 relating to U.S. Appl. No. 13/495,728, 21 pages.

(Continued)

*Primary Examiner* — Tse Chen
*Assistant Examiner* — Joanne Hoffman
(74) *Attorney, Agent, or Firm* — Senniger Powers LLP

(57) ABSTRACT

A system includes a handpiece configured to generate vibratory energy and a generator coupled to the handpiece. The generator includes a processing device and a memory device having encoded thereon computer-readable instructions that are executable by the processing device to perform functions including applying a first tuning signal to the handpiece. The first tuning signal has a first variable frequency within a predetermined frequency range. The functions further include detecting a first parameter and a second parameter of the ultrasonic handpiece in response to the first tuning signal, comparing the first parameter to the second parameter, and applying a second tuning signal to the ultrasonic handpiece. The second tuning signal has a second variable frequency within the predetermined frequency range.

15 Claims, 3 Drawing Sheets

(56) References Cited

U.S. PATENT DOCUMENTS

| | | | |
|---|---|---|---|
| 5,897,569 A | 4/1999 | Kellogg et al. | |
| 5,938,677 A * | 8/1999 | Boukhny et al. | 606/169 |
| 5,968,060 A | 10/1999 | Kellogg | |
| 5,997,533 A | 12/1999 | Kuhns | |
| 6,017,354 A | 1/2000 | Culp et al. | |
| 6,028,387 A * | 2/2000 | Boukhny | 310/316.01 |
| 6,053,906 A | 4/2000 | Honda et al. | |
| 6,217,591 B1 | 4/2001 | Egan et al. | |
| 6,352,532 B1 | 3/2002 | Kramer et al. | |
| 6,425,865 B1 | 7/2002 | Salcudean et al. | |
| 6,475,215 B1 | 11/2002 | Tanrisever | |
| 6,494,095 B1 | 12/2002 | Wan | |
| 6,602,193 B2 | 8/2003 | Chon | |
| 6,678,621 B2 * | 1/2004 | Wiener et al. | 702/75 |
| 6,679,899 B2 * | 1/2004 | Wiener et al. | 606/169 |
| 6,817,973 B2 | 11/2004 | Merril et al. | |
| 7,063,692 B2 | 6/2006 | Sakurai et al. | |
| 7,235,072 B2 | 6/2007 | Sartor et al. | |
| 7,273,483 B2 * | 9/2007 | Wiener et al. | 606/169 |
| 7,313,949 B2 | 1/2008 | Yorita et al. | |
| 7,476,233 B1 * | 1/2009 | Wiener et al. | 606/169 |
| 7,758,547 B2 | 7/2010 | Tonelli et al. | |
| 7,776,027 B2 | 8/2010 | Manna et al. | |
| 8,057,480 B2 | 11/2011 | Dorawa et al. | |
| 2002/0049464 A1 | 4/2002 | Donofrio et al. | |
| 2004/0001022 A1 | 1/2004 | Silzer, Jr. | |
| 2004/0115591 A1 | 6/2004 | Warner | |
| 2004/0211260 A1 * | 10/2004 | Girmonsky et al. | 73/579 |
| 2004/0267134 A1 * | 12/2004 | Hossack et al. | 600/459 |
| 2005/0288659 A1 * | 12/2005 | Kimura et al. | 606/27 |
| 2006/0229514 A1 * | 10/2006 | Wiener | 600/471 |
| 2006/0235424 A1 | 10/2006 | Vitale et al. | |
| 2007/0016235 A1 * | 1/2007 | Tanaka et al. | 606/169 |
| 2007/0031780 A1 | 2/2007 | Warner et al. | |
| 2007/0083209 A1 | 4/2007 | Schenberger et al. | |
| 2007/0123769 A1 | 5/2007 | Fuller et al. | |
| 2007/0196784 A1 * | 8/2007 | Bochi | 433/114 |
| 2008/0014627 A1 * | 1/2008 | Merchant | A61M 37/0092 435/259 |
| 2008/0039845 A1 | 2/2008 | Bonutti et al. | |
| 2008/0103515 A1 * | 5/2008 | Wiener | 606/169 |
| 2009/0024161 A1 * | 1/2009 | Bonutti | A61B 17/0401 606/213 |
| 2009/0036913 A1 * | 2/2009 | Wiener et al. | 606/169 |
| 2009/0098507 A1 | 4/2009 | Kirstgen | |
| 2009/0124585 A1 * | 5/2009 | Cross | B01D 9/0036 514/172 |
| 2009/0222037 A1 * | 9/2009 | Babaev et al. | 606/214 |
| 2009/0275864 A1 | 11/2009 | Hirai | |
| 2010/0004585 A1 | 1/2010 | Boukhny et al. | |
| 2010/0004586 A1 | 1/2010 | Boukhny et al. | |
| 2010/0094321 A1 | 4/2010 | Akahoshi et al. | |
| 2010/0174336 A1 | 7/2010 | Stein | |
| 2015/0099966 A1 | 4/2015 | Young et al. | |

OTHER PUBLICATIONS

Non-Final Office Action dated Jan. 5, 2015 relating to U.S. Appl. No. 13/495,735, 28 pages.
Non-Final Office Action for U.S. Appl. No. 13/495,728, dated Aug. 25, 2015, 13 pages.
Non-Final Office Action for U.S. Appl. No. 13/495,735, dated Nov. 2, 2015, 19 pages.
Non-Final Office Action dated Apr. 22, 2015 relating to U.S. Appl. No. 13/495,728, 17 pages.
Non-Final Office Action dated May 6, 2015 relating to U.S. Appl. No. 13/495,735, 20 pages.
Final Office Action dated Feb. 2, 2016 relating to U.S. Appl. No. 13/495,728, 9 pages.
Non-Final Office Action from U.S. Appl. No. 13/495,728, dated Nov. 3, 2016, 10 pages.
Non-Final Office Action from U.S. Appl. No. 13/495,728, dated Jul. 14, 2016, 10 pages.
Non-Final Office Action from U.S. Appl. No. 13/495,728, dated Jul. 7, 2017, 11 pages.

* cited by examiner

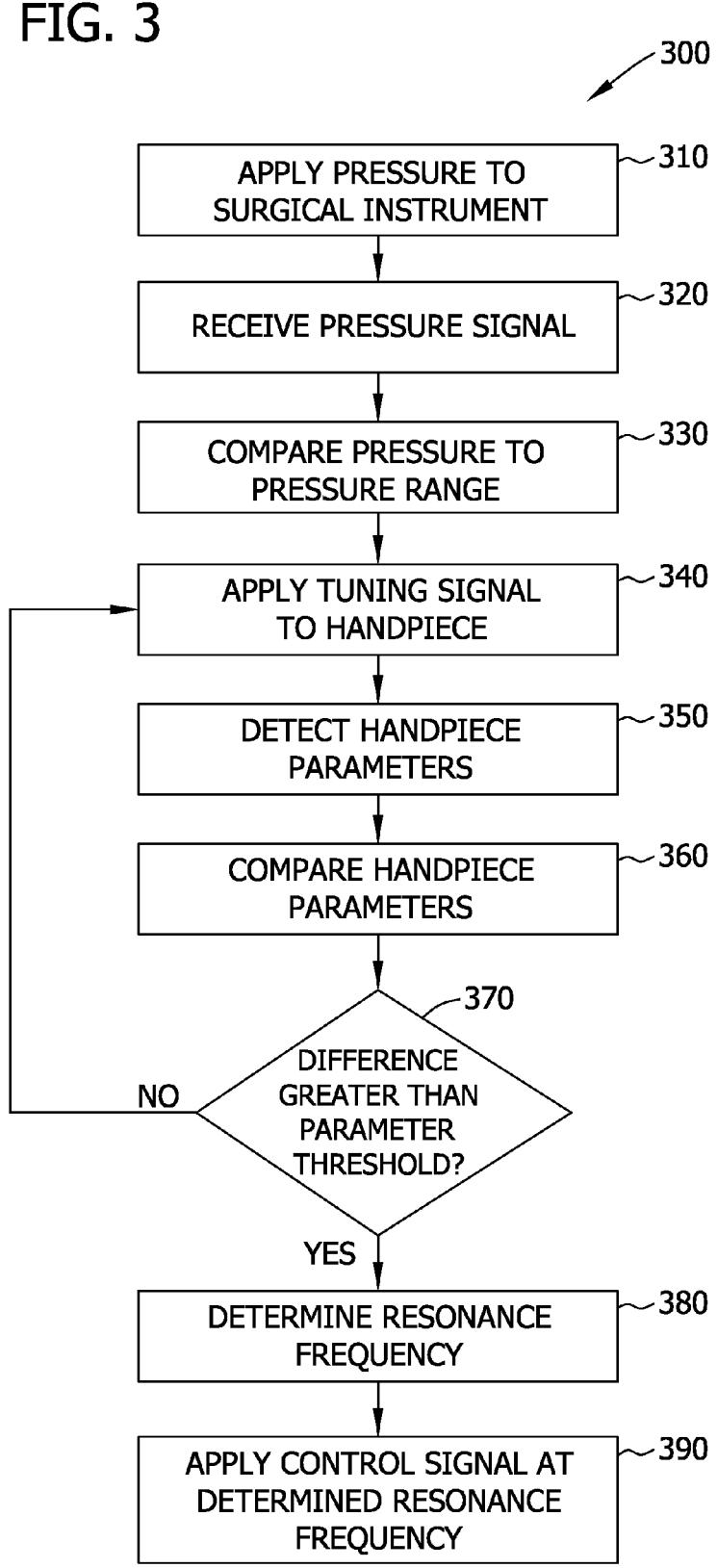

METHODS AND SYSTEMS FOR CONTROLLING AN ULTRASONIC HANDPIECE BASED ON TUNING SIGNALS

CROSS REFERENCE TO RELATED APPLICATIONS

This application claims priority to U.S. Provisional Patent Application No. 61/496,147 filed Jun. 13, 2011, U.S. Provisional Patent Application No. 61/526,182 filed Aug. 22, 2011, and U.S. Provisional Patent Application No. 61/526,207 filed Aug. 22, 2011, which are hereby incorporated by reference in their respective entireties.

BACKGROUND

The present disclosure relates generally to medical devices and, more particularly, to methods and systems for controlling an ultrasonic handpiece based on tuning signals.

Various types of known medical procedures involve repair and stabilization of body tissue. Such medical procedures may be utilized, for example, to treat conditions, such as, without limitation, a defect, damage, or fracture to bone, damaged or torn muscle, ligament or tendon, or separation of body tissues, etc. For example, fractured bones often involve stabilization of the bone in order to promote healing. Different bones and/or different types of fractures generally require unique procedures and/or surgical implements to facilitate stabilization of the body tissue. Accordingly, medical personnel employ a variety of surgical implements, such as screws, plates, and rods, to stabilize the bone across the fracture. In another example, further surgical implements may be used to anchor torn ligaments or tendons to other appropriate body tissue. As such, a variety of medical procedures and surgical implements are known to be used within the body of a patient to facilitate repair, stabilization, and/or healing of body tissue.

BRIEF SUMMARY

In one aspect, a method is provided for controlling an ultrasonic handpiece. The method includes applying a first tuning signal to the ultrasonic handpiece. The first tuning signal has a first variable frequency within a predetermined frequency range. The method further includes detecting a first parameter and a second parameter of the ultrasonic handpiece in response to the first tuning signal, comparing the first parameter to the second parameter, and applying a second tuning signal to the ultrasonic handpiece. The second tuning signal has a second variable frequency within the predetermined frequency range.

In another aspect, a surgical generator is provided for use with an ultrasonic handpiece. The surgical generator includes a processing device and a memory device having encoded thereon computer-readable instructions that are executable by the processing device to perform functions including applying a first tuning signal to the ultrasonic handpiece. The first tuning signal has a first variable frequency within a predetermined frequency range. The functions further include detecting a first parameter and a second parameter of the ultrasonic handpiece in response to the first tuning signal, comparing the first parameter to the second parameter, and applying a second tuning signal to the ultrasonic handpiece. The second tuning signal has a second variable frequency within the predetermined frequency range.

In yet another aspect, a system is provided. The system includes a handpiece configured to generate vibratory energy and a generator coupled to the handpiece. The generator includes a processing device and a memory device having encoded thereon computer-readable instructions that are executable by the processing device to perform functions including applying a first tuning signal to the handpiece. The first tuning signal has a first variable frequency within a predetermined frequency range. The functions further include detecting a first parameter and a second parameter of the ultrasonic handpiece in response to the first tuning signal, comparing the first parameter to the second parameter, and applying a second tuning signal to the ultrasonic handpiece. The second tuning signal has a second variable frequency within the predetermined frequency range.

The features, functions, and advantages described herein may be achieved independently in various embodiments of the present disclosure or may be combined in yet other embodiments, further details of which may be seen with reference to the following description and drawings.

BRIEF DESCRIPTION OF THE DRAWINGS

FIGS. 1-3 show exemplary embodiments of the methods and systems described herein.

FIG. 1 is a schematic illustration of an exemplary surgical system;

FIG. 2 is a cross-sectional view of an exemplary ultrasonic handpiece that may be used with the surgical system shown in FIG. 1; and FIG. 3 is a flowchart of an exemplary method of controlling the surgical system shown in FIG. 1.

Although specific features of various embodiments may be shown in some drawings and not in others, this is for convenience only. Any feature of any drawing may be referenced and/or claimed in combination with any feature of any other drawing.

DETAILED DESCRIPTION

The present disclosure relates generally to medical devices and, more particularly, to methods and systems for controlling ultrasonic handpieces based on tuning signals. In one embodiment, a first tuning signal is applied to a handpiece, and a first parameter and a second parameter of the ultrasonic handpiece are detected in response to the first tuning signal. The first parameter is compared to the second parameter, and a second tuning signal is applied to the ultrasonic handpiece when the difference between the first parameter and the second parameter is less than a predetermined parameter threshold.

Exemplary technical effects of the methods and systems described herein may include at least one of (a) receiving a pressure signal from the pressure sensor; (b) determining a pressure applied between an ultrasonic handpiece and a surgical implement; (c) comparing the pressure between the ultrasonic handpiece and the surgical implement to a predetermined pressure range; (d) applying a first tuning signal to the ultrasonic handpiece; (e) detecting a first parameter and a second parameter of the ultrasonic handpiece in response to the first tuning signal; (f) comparing the first parameter to the second parameter; (g) determining whether a difference between the first parameter and the second parameter is less than a predetermined parameter threshold; (h) applying a second tuning signal to the ultrasonic handpiece; (i) detecting a third parameter and a fourth parameter of the ultrasonic handpiece in response to the second tuning signal; (j) comparing the third parameter to the fourth parameter; (k) determining whether a difference between the third parameter and the fourth parameter is less than a predetermined parameter threshold; and (l) applying a third tuning signal to the ultrasonic handpiece, the third tuning signal having a third variable frequency within the predetermined frequency range.

As used herein, an element or step recited in the singular and preceded with the word "a" or "an" should be understood as not excluding plural elements or steps unless such exclusion is explicitly recited. Moreover, references to "one embodiment" and/or the "exemplary embodiment" are not intended to be interpreted as excluding the existence of additional embodiments that also incorporate the recited features.

Figure 1:
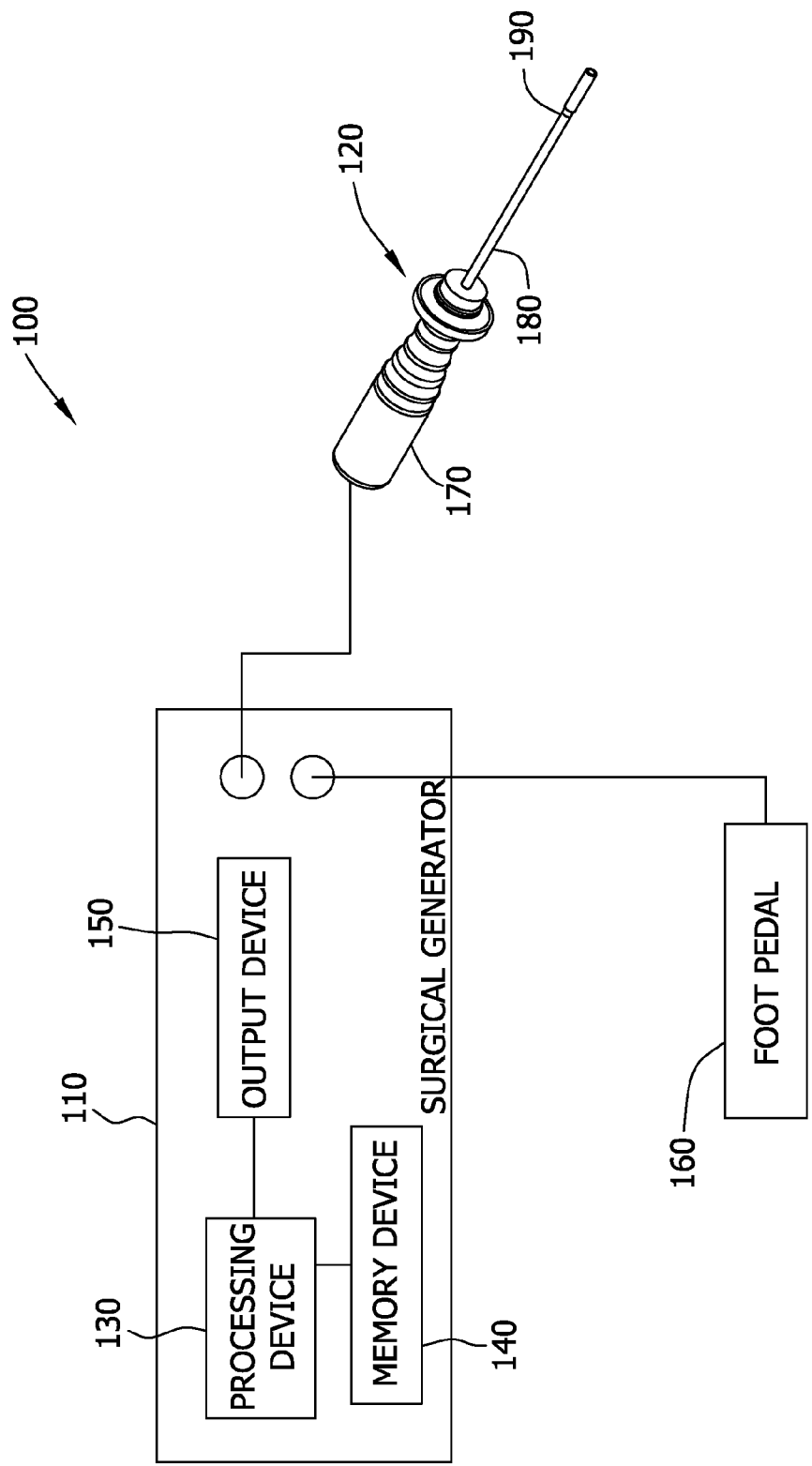

FIG. 1 shows an exemplary surgical system 100 including a surgical generator 110 and a handpiece 120, which may be removably coupled to surgical generator 110. Alternatively, surgical generator 110 may be integrated with handpiece 120. As used herein, surgical and/or surgery are used to generally refer to any medical procedure involving a patient (a human being, an animal, etc.) and may include in-patient procedures, out-patient procedures, invasive procedures, non-invasive procedures, and/or minimally invasive procedures. In at least some embodiments, surgical implements (not shown) are disposed within the patient's body in orientations suitable for a respective medical procedure, such as a fracture stabilization procedure. Surgical implements may include implants or other suitable medical devices such as, without limitation, pins, screws, fasteners, dowels, rods, plates, and/or anchors. Moreover, as used herein, handpiece is used to generally refer to a housing, casing, frame, holder, and/or support that can be manually carried and manipulated during a medical procedure involving a patient.

In the exemplary embodiment, surgical generator 110 includes a processing device 130 and a memory device 140 coupled to processing device 130. Processing device 130 may include, without limitation, a microcontroller, a microprocessor, a programmable gate array, an application specific integrated circuit (ASIC), a logic circuit, and/or any other circuit, integrated or otherwise, suitable to perform as described herein. Memory device 140 includes one or more devices operable to enable information such as executable instructions and/or other data to be stored and/or retrieved. Memory device 140 may include one or more computer readable media including, without limitation, hard disk storage, optical drive/disk storage, removable disk storage, flash memory, non-volatile memory, ROM, electrically-erasable programmable read-only memory (EEPROM), and/or random access memory (RAM). Memory device 140 is used to store one or more of predetermined thresholds, resonant frequencies, settings specific to handpiece 120, and/or executable instructions.

In the exemplary embodiment, surgical generator 110 includes an output device 150 for example, a cathode ray tube (CRT), a liquid crystal display (LCD), an LED display, an "electronic ink" display, and/or other device suitable to display information to an operator. Additionally, output device 150 may include an audio output device (e.g., a speaker, etc.) to indicate verbal instructions, alerts, and/or warnings to the operator.

In the exemplary embodiment, surgical generator 110 includes one or more input devices, such as, without limitation, a button, a pedal, a knob, a keypad, a pointing device, a mouse, a touch sensitive panel (e.g., a touch pad or a touchscreen), a gyroscope, a position detector, and/or an audio input (e.g., a microphone). For example, in the exemplary embodiment, a foot pedal 160 is removably coupled to surgical generator 110 to enable an operator to provide input to surgical generator 110. In one embodiment, the input device is integrated with surgical generator 110. In another embodiment, the input device is remote from surgical generator 110 and coupled thereto.

Different types of handpieces 120 may be used with surgical generator 110 based on a type of medical procedure and/or a type of surgical implement. For example, various handpieces 120 may have different configurations and/or properties (e.g., acoustical characteristics, resonance frequency), and/or various surgical implements may require handpieces 120 of different sizes and/or configurations. In the exemplary embodiment, an identifier (not shown) enables surgical generator 110 to automatically identify handpiece 120. For example, surgical generator 110 may read and/or detect a resistance identification, an RFID tag, and/or another identifying component to differentiate handpiece 120 from other handpieces 120. Additionally or alternatively, an operator may manually identify handpiece 120. In at least some embodiments, the identifier is associated with multiple medical procedures and/or surgical implements. In such embodiments, the operator may provide, and surgical generator 110 may receive, one or more inputs to select a medical procedure to be performed and/or a surgical implement to be interfaced.

In this manner, one or more handpieces 120 may be replaced between medical procedures. In at least some embodiments, handpiece 120 is removed after each patient such that handpiece 120 may be autoclaved between medical procedures to substantially ensure sterility for one or more subsequent patients. Accordingly, handpiece 120 is configured to withstand multiple autoclave procedures.

In the exemplary embodiment, handpiece 120 includes an outer housing 170, a horn 180 extending longitudinally from outer housing 170, an end effector 190 coupled to horn 180, and a sheath 195 (shown in FIG. 2) coupled to outer housing 170 and extending about and spaced radially from horn 180 and/or end effector 190. In the exemplary embodiment, horn 180 and/or end effector 190 are sized and/or configured to slide within sheath 195. In at least some embodiments, end effector 190 is integrated with horn 180. In the exemplary embodiment, handpiece 120 is useable to affect one or multiple surgical implements during a surgery. More specifically, handpiece 120 applies vibratory energy, such as ultrasonic energy, to one or more of the surgical implements to form a weld between the surgical implements.

In the exemplary embodiment, handpiece 120 is configured to provide an ergonomic interaction with an operator including, without limitation, a surgeon, a doctor, a surgery assistant, a nurse, a veterinarian, and/or other medical personnel present for a medical procedure. Other shapes and/or sizes of handpiece 120 may be included in other surgical system embodiments. In at least some embodiments, handpiece 120 is configured to interact with and/or be utilized by a robotic arm for robotic and/or remote control of handpiece 120.

Figure 2:
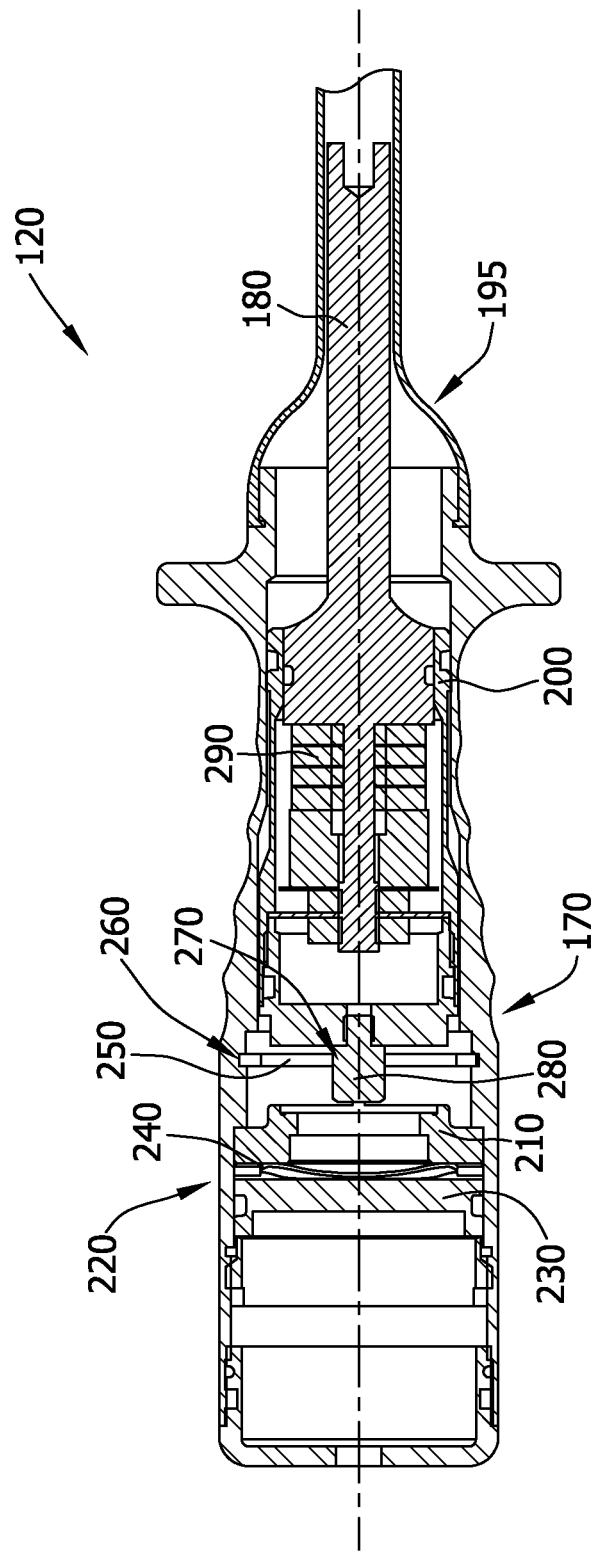

FIG. 2 is a cross-sectional view of handpiece 120. In the exemplary embodiment, outer housing 170 houses at least an inner housing 200 and at least a portion of a transducer system or, more specifically, load cell 210. In the exemplary embodiment, load cell 210 is configured to detect a first force and/or pressure applied to load cell 210 and transmit to surgical generator 110 (shown in FIG. 1) a pressure signal associated with and/or indicative of the first pressure. The first pressure is associated with a force and/or pressure between end effector 190 (shown in FIG. 1) and a surgical implement in contact with end effector 190, which, in turn, directly applies a force and/or pressure to horn 180.

In the exemplary embodiment, a biasing mechanism 220 is positioned within outer housing 170 to counteract, reduce and/or limit the first pressure applied to load cell 210. More specifically, biasing mechanism 220 is moveable between an unflexed or home position and a flexed position. As the first pressure applied to load cell 210 generally increases, in the exemplary embodiment, biasing mechanism 220 moves towards the flexed position. Conversely, as the first pressure applied to load cell 210 generally decreases, in the exemplary embodiment, biasing mechanism 220 moves towards the home position. In the exemplary embodiment, biasing mechanism 220 includes a spring plate 230 and a wave spring 240 that is configured to compress as the first pressure increases and/or expand as the first pressure decreases. Alternatively, any type of biasing mechanism 220 may be used that enables handpiece 120 to function as described herein.

In the exemplary embodiment, outer housing 170 defines a cavity therein that is sized and/or configured such that inner housing 200 is retained within outer housing 170. More specifically, outer housing 170 and/or inner housing 200 includes at least one retaining mechanism 250 that facilitates counteracting, reducing, and/or limiting the first pressure applied to load cell 210. For example, in the exemplary embodiment, retaining mechanism 250 is positioned within outer housing 170 between inner housing 200 and load cell 210 to prevent and/or limit inner housing 200 from moving towards load cell 210 beyond a predetermined position. In the exemplary embodiment, a portion of retaining mechanism 250 is positioned at the predetermined position within a groove 260 defined by an inner surface of outer housing 170. In the exemplary embodiment, retaining mechanism 250 includes an opening 270 extending longitudinally therethrough, and a standoff 280 coupled to inner housing 200 extends through opening 270 such that standoff 280 is configured to directly apply the first pressure to load cell 210. Alternatively, any type of retaining mechanism 250 may be used that enables handpiece 120 to function as described herein.

In the exemplary embodiment, inner housing 200 houses at least a portion of horn 180 and at least a portion of a transducer system or, more specifically, vibrating mechanism 290 coupled to horn 180. In the exemplary embodiment, vibrating mechanism 290 is a piezoelectric stack that is configured to generate vibratory energy (e.g., ultrasonic energy) upon receiving a control signal to activate a weld cycle. In the exemplary embodiment, horn 180 is configured to transmit the vibratory energy to an operative site. More specifically, horn 180 is coupleable to end effector 190 such that the vibratory energy is transmitted to end effector 190 through horn 180. Alternatively, the vibratory energy may be transmitted to the operative site using any mechanism that enables handpiece 120 to function as described herein.

The transducer system includes at least vibrating mechanism 290 and load cell 210. In this manner, the transducer system is configured to detect the first pressure, transmit the pressure signal, and generate ultrasonic vibratory energy. In the exemplary embodiment, vibrating mechanism 290 is remote from load cell 210. Alternatively, vibrating mechanism 290 may be adjacent and/or integrated with load cell 210.

In at least some embodiments, handpiece 120 includes a series of electrical contacts that are coupled to vibrating mechanism 290. In such embodiments, the electrical contacts are moveable between a closed configuration and an open configuration such that the electrical contacts are electrically and/or communicatively coupled and/or decoupled, respectively. In such embodiments, as pressure applied to end effector 190, horn 180, and/or load cell 210 generally increases, the electrical contacts move toward the closed configuration, thereby coupling surgical generator 110 to vibrating mechanism 290. Conversely, as pressure applied to end effector 190, horn 180, and/or load cell 210 generally decreases, in such embodiments, the electrical contacts move toward the open configuration, thereby decoupling surgical generator 110 from vibrating mechanism 290. Alternatively, the electrical contacts may be positioned anywhere within handpiece 120 that enables surgical system 100 to function as described herein.

FIG. 3 is a flowchart of an exemplary method 300 of controlling surgical system 100. During operation, in the exemplary embodiment, handpiece 120 is identified based on an identifier and/or selected based on a type of medical procedure and/or surgical implement. In the exemplary embodiment, surgical generator 110 retrieves one or more settings associated with handpiece 120, the medical procedure, and/or the surgical implement from memory device 140 based on the identifier. The settings are used by surgical generator 110 to provide one or more control signals to handpiece 120. Settings retrieved from memory device 140 may include, without limitation, frequencies, voltages, currents, and/or control algorithms. For example, in the exemplary embodiment, the setting retrieved from memory device 140 includes a predetermined force and/or pressure range that enables a resonant frequency and/or other parameter associated with handpiece 120 to be determined, as described below.

Upon identification and/or selection of handpiece 120 and retrieval of one or more settings from memory device 140, surgical system 100 is generally ready to affect the surgical implement. In the exemplary embodiment, end effector 190 is positioned at least partially within the patient and in contact with the surgical implement. More specifically, the operator uses handpiece 120 to apply 310 force and/or pressure to the surgical implement, which, in turn, applies a force and/or pressure to horn 180 and inner housing 200. As a result, standoff 280 applies the first pressure to load cell 210, which detects the first pressure and transmits the pressure signal from handpiece 120 to surgical generator 110.

In the exemplary embodiment, surgical generator 110 receives 320 the pressure signal from handpiece 120 and compares 330 the pressure between end effector 180 and the surgical implement, as indicated by the pressure signal, to the pressure range. More specifically, surgical generator 110 determines a pressure based on the pressure signal, and the pressure is compared to the pressure range. When the pressure is within the pressure range, surgical generator 110 transmits and/or applies 340 a first tuning signal to handpiece 120. In the exemplary embodiment, surgical generator 110 varies the frequency of the first tuning signal within a predetermined frequency range retrieved from memory device 140. For example, when surgical generator 110 has identified surgical handpiece 120 as a 20 kHz surgical handpiece, the predetermined frequency range may be between approximately 19.5 kHz and approximately 20.7 kHz. Alternatively, the predetermined frequency range may be associated with any frequency that enables handpiece 120 to function as described herein.

As the frequency of the first tuning signal is being varied, surgical generator 110 detects 350 parameters of handpiece

120 including, without limitation, impedance, phase, and/or frequency of handpiece 120. For example, in the exemplary embodiment, surgical generator 110 detects a first impedance and a second impedance. More specifically, the first impedance is an upper or maximum impedance at a first frequency and the second impedance is a lower or minimum impedance at a second frequency. Alternatively, surgical generator 110 may detect 350 any parameter associated with any frequency that enables handpiece 120 to function as described herein.

In the exemplary embodiment, surgical generator 110 compares 360 the first parameter to the second parameter, and determines 370 whether a difference between the first parameter and the second parameter is less than a predetermined parameter threshold retrieved from memory device 140. When the difference between the first and second parameters is determined 370 to be at and/or above the parameter threshold, in the exemplary embodiment, surgical generator 110 identifies and/or determines 380 the second frequency as the resonance frequency of handpiece 120. Alternatively, surgical generator 110 may determine 380 any resonance frequency that enables handpiece 120 to function as described herein.

Conversely, when the difference between the first and second parameters is determined 370 to be less than the parameter threshold, in the exemplary embodiment, surgical generator 110 transmits and/or applies 340 a second tuning signal to handpiece 120. In the exemplary embodiment, surgical generator 110 varies the frequency of the second tuning signal within the predetermined frequency range retrieved from memory device 140. In the exemplary embodiment, the first tuning signal and the second tuning signal are the same and/or substantially similar. Alternatively, surgical generator 110 may apply any tuning signal that enables handpiece 120 to function as described herein.

As the frequency of the second tuning signal is being varied, surgical generator 110 detects 350 parameters of handpiece 120 including, without limitation, impedance, phase, and/or frequency of handpiece 120. For example, in the exemplary embodiment, surgical generator 110 detects a third impedance and a fourth impedance. More specifically, the third impedance is an upper or maximum impedance at a third frequency and the fourth impedance is a lower or minimum impedance at a fourth frequency. Alternatively, surgical generator 110 may detect 350 any parameter associated with any frequency that enables handpiece 120 to function as described herein.

In the exemplary embodiment, surgical generator 110 compares 360 the third parameter to the fourth parameter, and determines 370 whether a difference between the third parameter and the fourth parameter is less than a predetermined parameter threshold retrieved from memory device 140. When the difference between the third and fourth parameters is determined 370 to be at and/or above the parameter threshold, in the exemplary embodiment, surgical generator 110 determines 380 the fourth frequency as the resonance frequency of handpiece 120. Alternatively, surgical generator 110 may determine 380 any resonance frequency that enables handpiece 120 to function as described herein.

Conversely, when the difference between the third and fourth parameters is determined 370 to be less than the parameter threshold, surgical generator 110 may repeat the process any number of times until a resonance frequency of handpiece 120 is determined. In the exemplary embodiment, surgical generator 110 presents and/or generates a warning to the operator indicating a failure to determine a resonance frequency after the process is repeated a predetermined number of times without determining a resonance frequency of handpiece 120.

When a resonance frequency of handpiece 120 is determined 380, surgical generator 110 transmits and/or applies 390 a control signal at the determined resonance frequency to handpiece 120. More specifically, vibrating mechanism 290 receives the control signal to activate a weld cycle and generates vibratory energy upon receiving the control signal. The vibratory energy is transferred through horn 180 and end effector 190 to the surgical implement. The vibratory energy propagates through the surgical implement to vibrate the surgical implement and an adjacent surgical implement, which generates heat and a weld therebetween.

In at least some embodiments, vibrating mechanism 290 receives a control signal associated with a tuning signal that is not associated with the resonance frequency of handpiece 120. In such embodiments, the vibratory energy may be insufficient to generate a weld between adjacent surgical implements. The vibratory energy, however, may be sufficient to re-seat the surgical implement within an aperture defined in handpiece 120, clear debris between handpiece 120 and the surgical implement, and/or overcome another impediment between handpiece 120 and the surgical implement.

The embodiments described herein relate generally to medical devices and, more particularly, to methods and systems for controlling an ultrasonic handpiece based on tuning signals. The embodiments described herein apply tuning signals to an ultrasonic handpiece to determine a resonance frequency of the ultrasonic handpiece. As such, the embodiments described herein facilitate creating effective and/or reliable welds, thereby improving a repair, stabilization, and/or healing time associated with the patient.

Exemplary embodiments of ultrasonic handpieces are described above in detail. The methods and systems are not limited to the specific embodiments described herein, but rather, components of systems and/or steps of the method may be utilized independently and separately from other components and/or steps described herein. Each method step and each component may also be used in combination with other method steps and/or components. Although specific features of various embodiments may be shown in some drawings and not in others, this is for convenience only. Any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of controlling an ultrasonic handpiece, said method comprising:
   sensing a pressure between the ultrasonic handpiece and a surgical implement disposed within the body of a patient;
   comparing the sensed pressure between the ultrasonic handpiece and the surgical implement to a predetermined pressure range to determine if the sensed pressure is within the predetermined pressure range, the predetermined pressure range indicating that the sensed pressure between the ultrasonic handpiece and the surgical implement is ready for welding;

applying a first tuning signal to the ultrasonic handpiece only when the pressure between the ultrasonic handpiece and the surgical implement is determined to be within the predetermined pressure range, the first tuning signal having a first variable frequency within a predetermined frequency range between 19.5 kHz and 20.7 kHz;

detecting a first impedance and a second impedance of the ultrasonic handpiece in response to the first tuning signal;

comparing the first impedance to the second impedance;

applying a second tuning signal to the ultrasonic handpiece, the second tuning signal having a second variable frequency within the predetermined frequency range; and transferring, when the pressure between the ultrasonic handpiece and the surgical implement has settled within the predetermined pressure range for at least a predetermined settling interval, vibratory energy through the ultrasonic handpiece to the surgical implement to form a weld at the surgical implement for stabilizing body tissue with the weld, wherein the predetermined settling interval is 2 seconds.

2. The method of claim 1 wherein said comparing the first impedance to the second impedance comprises determining whether a difference between the first impedance and the second impedance is less than a predetermined threshold.

3. The method of claim 1 further comprising:
detecting a third impedance and a fourth impedance of the ultrasonic handpiece in response to the second tuning signal;
comparing the third impedance to the fourth impedance; and
applying a third tuning signal to the ultrasonic handpiece, the third tuning signal having a third variable frequency within the predetermined frequency range.

4. The method of claim 3 wherein said comparing the third impedance to the fourth impedance comprises determining whether a difference between the third impedance and the fourth impedance is less than a predetermined threshold.

5. A surgical generator for use with an ultrasonic handpiece, said surgical generator comprising:
a processing device; and
a memory device comprising a tangible, non-transitory computer readable medium having encoded thereon computer-readable instructions that are executable by the processing device to perform functions comprising:
receiving a pressure signal from a pressure sensor indicative of a pressure between the ultrasonic handpiece and a surgical implement disposed within a body of a patient;
determining a sensed pressure between the ultrasonic handpiece and the surgical implement based on the pressure signal;
comparing the sensed pressure between the ultrasonic handpiece and the surgical implement to a predetermined pressure range to determine if the sensed pressure is within the predetermined pressure range, the predetermined pressure range indicating that the sensed pressure between the ultrasonic handpiece and the surgical implement is ready for welding;
applying a first tuning signal to the ultrasonic handpiece only when the pressure between the ultrasonic handpiece and the surgical implement is determined to be within the predetermined pressure range, the first tuning signal having a first variable frequency within a predetermined frequency range between 19.5 kHz and 20.7 kHz;
detecting a first impedance and a second impedance of the ultrasonic handpiece in response to the first tuning signal;
comparing the first impedance to the second impedance;
applying a second tuning signal to the ultrasonic handpiece, the second tuning signal having a second variable frequency within the predetermined frequency range; and
causing vibratory energy to be transferred, when the pressure between the ultrasonic handpiece and the surgical implement has settled within the predetermined pressure range for at least a predetermined settling interval, through the ultrasonic handpiece to the surgical implement to form a weld at the surgical implement for stabilizing body tissue with the weld, wherein the predetermined settling interval is 2 seconds.

6. The surgical generator in accordance with claim 5, wherein said comparing the first impedance to the second impedance comprises determining whether a difference between the first impedance and the second impedance is less than a predetermined threshold.

7. The surgical generator in accordance with claim 5, wherein the functions performed by the processing device further comprise:
detecting a third impedance and a fourth impedance of the ultrasonic handpiece in response to the second tuning signal;
comparing the third impedance to the fourth impedance; and
applying a third tuning signal to the ultrasonic handpiece, the third tuning signal having a third variable frequency within the predetermined frequency range.

8. The surgical generator in accordance with claim 7, wherein said comparing the third impedance to the fourth impedance comprises determining whether a difference between the third impedance and the fourth impedance is less than a predetermined threshold.

9. A system comprising:
a handpiece configured to generate vibratory energy, the handpiece comprising a pressure sensor adapted to produce a pressure signal indicative of a pressure between the handpiece and a surgical implement; and
a generator coupled to the handpiece, the generator comprising a processing device and a memory device having encoded thereon computer-readable instructions that are executable by the processing device to perform functions comprising:
receiving a pressure signal from the pressure sensor indicative of a pressure between the handpiece and a surgical implement disposed within a body of a patient;
determining a sensed pressure between the handpiece and the surgical implement based on the pressure signal;
comparing the sensed pressure between the handpiece and the surgical implement to a predetermined pressure range to determine if the sensed pressure is within the predetermined pressure range, the predetermined pressure range indicating that the sensed pressure between the handpiece and the surgical implement is ready for welding;

applying a first tuning signal to the handpiece only when the pressure between the handpiece and the surgical implement is determined to be within the predetermined pressure range, the first tuning signal having a first variable frequency within a predetermined frequency range between 19.5 kHz and 20.7 kHz;

detecting a first impedance and a second impedance of the handpiece in response to the first tuning signal;

comparing the first impedance to the second impedance;

applying a second tuning signal to the handpiece, the second tuning signal having a second variable frequency within the predetermined frequency range; and transferring, when the pressure between the handpiece and the surgical implement has settled within the predetermined pressure range for at least a predetermined settling interval, vibratory energy through the handpiece to the surgical implement to form a weld at the surgical implement for stabilizing body tissue with the weld, wherein the predetermined settling interval is 2 seconds.

10. The system in accordance with claim 9, wherein said comparing the first impedance to the second impedance comprises determining whether a difference between the first impedance and the second impedance is less than a predetermined threshold.

11. The system in accordance with claim 9, wherein the functions performed by the processing device further comprise:

detecting a third impedance and a fourth impedance of the handpiece in response to the second tuning signal;

comparing the third impedance to the fourth impedance; and applying a third tuning signal to the handpiece, the third tuning signal having a third variable frequency within the predetermined frequency range.

12. The system in accordance with claim 11, wherein said comparing the third impedance to the fourth impedance comprises determining whether a difference between the third impedance and the fourth impedance is less than a predetermined threshold.

13. The method of claim 1 further comprising applying a resonance frequency to the ultrasonic handpiece to form a weld at the surgical implement.

14. The method of claim 5 further comprising applying a resonance frequency to the ultrasonic handpiece to form a weld at the surgical implement.

15. The method of claim 9 further comprising applying a resonance frequency to the ultrasonic handpiece to form a weld at the surgical implement.

* * * * *